United States Patent

Zierke et al.

Patent Number: 5,156,669
Date of Patent: Oct. 20, 1992

[54] 5-(1,2,4-TRIAZOL-1-YLMETHYL)-ISOXAZOLINES

[76] Inventors: Thomas Zierke, 12 Akazienstrasse, 6737 Boehl-Iggelheim; Thomas Kuekenhoehner, 2 Seidelstrasse, 6710 Frankenthal; Juergen Frank, 2 Baltenweg, 6703 Limburgerhof; Eberhard Ammermann, 3 Sachsenstrasse, 6700 Ludwigshafen; Gisela Lorenz, 13 Erlenweg, 6730 Neustadt, all of Fed. Rep. of Germany

[21] Appl. No.: 682,296

[22] Filed: Apr. 9, 1991

[30] Foreign Application Priority Data

Apr. 28, 1990 [DE] Fed. Rep. of Germany ....... 4013723

[51] Int. Cl.$^5$ .................. C07D 413/14; C07D 216/04; A01N 43/74
[52] U.S. Cl. ............................ 71/92; 71/77; 514/256; 514/340; 514/378; 544/333; 546/276; 548/240
[58] Field of Search ............ 548/240; 544/333; 546/276; 71/92, 77; 514/256, 340, 378

[56] References Cited

U.S. PATENT DOCUMENTS

| | | | |
|---|---|---|---|
| 4,079,062 | 3/1978 | Van Reet et al. | 260/308 |
| 4,315,017 | 2/1982 | Linhart et al. | 424/269 |
| 4,719,306 | 1/1988 | St. Georgiev et al. | 548/240 |
| 4,727,157 | 2/1988 | St. Georgiev et al. | 548/240 |
| 4,749,793 | 6/1988 | Georgiev et al. | 548/240 |
| 4,777,263 | 10/1988 | Georgiev et al. | 548/240 |
| 4,780,471 | 10/1988 | Maeda et al. | 514/383 |
| 4,957,931 | 9/1990 | Bowman | 514/373 |

FOREIGN PATENT DOCUMENTS

| | | | |
|---|---|---|---|
| 0094167 | 11/1983 | European Pat. Off. | 548/240 |
| 0241232 | 10/1987 | European Pat. Off. | 548/240 |
| 0257391 | 1/1988 | European Pat. Off. | 548/240 |
| 0257351 | 2/1988 | European Pat. Off. | 548/240 |
| 2551560 | 3/1978 | Fed. Rep. of Germany | 260/308 |
| 2833194 | 2/1982 | Fed. Rep. of Germany | 424/269 |

OTHER PUBLICATIONS

Chemical Abstracts, vol. 99, entry 194892e (1983) Stotskii et al. p.748.
Chemical Abstracts, vol. 101, entry 171181t (1984) Vereshchagin et al. p. 696.

Primary Examiner—Mary C. Lee
Assistant Examiner—Joseph K. McKane

[57] ABSTRACT 5-(1,2,4-Triazol-1-yl-methyl)-isoxazolines I

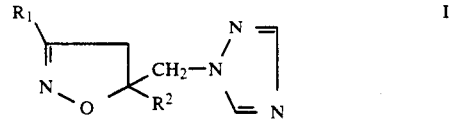

where $R^1$ and $R^2$ are each H, alkoxyalkyl, haloalkyl, alkyl, cycloalkylalkyl, phenylalkyl, naphthylalkyl, cycloalkyl, phenyl, naphthyl or hetaryl, where the aryl and hetaryl moieties of the stated substituents may furthermore carry an unsubstituted or halogen-substituted phenyl or phenoxy radical or up to 3 of the following radicals: halogen, CN, $NO_2$, alkyl, haloalkyl or alkoxy, and the salts and metal complexes of I are suitable as fungicides and for regulating plant growth.

7 Claims, No Drawings

5-(1,2,4-TRIAZOL-1-YLMETHYL)-ISOXAZOLINES

The present invention relates to novel 5-(1,2,4-triazol-1-ylmethyl)-isoxazolines of the general formula I

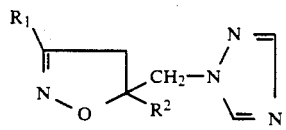

where $R^1$ and $R^2$ are each hydrogen, $C_1$-$C_4$-alkoxy-$C_1$-$C_4$-alkyl, partially or completely halogenated $C_1$-$C_6$-alkyl or $C_1$-$C_6$-alkyl which may carry a $C_3$-$C_8$-cycloalkyl, phenyl or naphthyl radical, or are each $C_3$-$C_8$-cycloalkyl, phenyl or naphthyl, or a $C_5$- or $C_6$-hetaryl group which contains 3 nitrogen atoms, not more than 2 of which may be adjacent, or up to 2 of the following hetero atoms: oxygen, sulfur and/or nitrogen, where 2 oxygen and/or sulfur atoms may not be adjacent, and where the phenyl, naphthyl and hetaryl moieties of the stated groups may furthermore each carry a phenyl or phenoxy radical having up to 3 halogen substituents, or up to 3 of the following radicals: halogen, cyano, nitro, $C_1$-$C_4$-alkyl, partially or completely halogenated $C_1$-$C_4$-alkyl or $C_1$-$C_4$-alkoxy, and the plant-tolerated mineral acid salts I.HX and metal complexes of I.

The present invention furthermore relates to a process for the preparation of these compounds, their use as fungicides and for regulating plant growth, and fungicides and plant growth regulators which contain these compounds as active substances.

The present invention furthermore relates to 2-(1,2,4-triazol-1-ylmethyl)-alkenes of the formula III

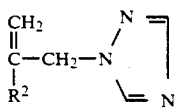

where $R^2$ has the meanings stated in claim 1, with the exception of hydrogen, methyl, phenyl, halophenyl, dihalophenyl, 3-trifluoromethylphenyl and $C_1$-$C_4$-alkylphenyl.

DE-A 25 51 560 discloses substituted 2-phenyl-2-(1,2,4-triazol-1-ylmethyl)-1,3-dioxolanes and EP-A 094 167 discloses 4-phynyl-4-(1,2,4-triazol-1-ylmethyl)-1,3-dioxolanes having fungicidal and plant growth-regulating properties. Furthermore, the stated European publication describes 1-(1,2,4-triazol-1-ylmethyl)-styrenes as intermediates for the preparation of the 1,3-dioxolanes stated there. The styrene derivatives are also said to have a fungicidal action. Unsubstituted 1-(1,2,4-triazol-1-ylmethyl)-styrene and its synergistic action in insecticides are described in DE-A 28 33 194.

Moreover, EP-A 257 351, EP-A 257 391 and U.S. Pat. No. 4,749,793 disclose fungicidal 3-phenyl-3-(triazol-ylmethyl)- and 3-phenyl-3-(1,3-diazolylmethyl-)isoxazolidines having a methyl or benzyl group on the nitrogen of the (saturated) isoxazolidine parent structure.

However, the fungicidal and plant growth-regulating properties of these compounds may be satisfactory only to a limited extent, particularly in the case of low application rates and concentrations.

It is an object of the present invention to provide novel substances which have fungicidal and/or plant growth-regulating properties.

We have found that this object is achieved by the 5-(1,2,4-triazol-1-ylmethyl)-isoxazolines of the formula I which are defined at the outset.

We have also found novel intermediates of the formula III for the preparation of the 5-(1,2,4-triazol-1-ylmethyl)-isoxazolines.

The substituents $R^1$ and $R^2$ in the novel compounds I and $R^2$ in the intermediates III have the following specific meanings:

hydrogen;

partially or completely halogenated, straight-chain or branched $C_1$-$C_6$-alkyl, in particular $C_1$-$C_4$-alkyl, such as chloromethyl, dichloromethyl, trichloromethyl, bromomethyl, 1-chloroethyl, pentafluoroethyl, 2-chloro-1,1,2-trifluoroethyl or 4-chlorobut-1-yl; straight-chain or branched $C_1$-$C_4$-alkoxy-$C_1$-$C_4$-alkyl, in particular $C_1$-$C_4$-alkoxy-$C_1$- or $C_2$-alkyl, such as methoxymethyl, ethoxymethyl, 2-ethoxyethyl, 2-butoxyethyl or 2-tert-butoxyethyl;

straight-chain or branched $C_1$-$C_6$-alkyl, in particular $C_1$-$C_4$-alkyl, such as methyl, ethyl, isopropyl or tert-butyl; phenyl, naphthyl or $C_3$-$C_8$-cycloalkyl, or straight-chain or branched $C_1$-$C_6$-alkyl, in particular $C_1$-$C_4$-alkyl, which carries a phenyl, naphthyl or $C_3$-$C_8$-cycloalkyl radical, where the cyclic radicals may each furthermore carry a phenyl or phenoxy radical which is unsubstituted or substituted by 1-3 halogen atoms or may carry not more than 2 of the following substituents: halogen, such as fluorine, chlorine or bromine, cyano, nitro, straight-chain or branched $C_1$-$C_4$-alkyl, such as methyl, ethyl, isopropyl or tert-butyl, straight-chain or branched, partially or completely halogenated $C_1$-$C_4$-alkyl, such as chloromethyl, trichloromethyl, trifluoromethyl, bromomethyl, 1-chloroethyl, pentafluoroethyl, 2-chloro-1,1,2-trifluoroethyl or 4-chloro-but-1-yl, or straight-chain or branched $C_1$-$C_4$-alkoxy, such as methoxy, ethoxy, isopropoxy or tert-butoxy;

preferred groups are cyclopropyl, 1-methylcycloprop-1-yl, cyclobutyl, cyclopentyl, cyclohexyl, 2-methylcyclohexyl, 3-isopropylcyclohexyl, 4-tert-butylcyclohexyl, 2-isopropyl-5-methylcyclohex-1-yl, cycloheptyl, cyclooctyl, cyclopropylmethyl, 1-cyclopropylethyl, 2-cyclopropylethyl, cyclopentylmethyl, 1-cyclopentylethyl, 1-cyclohexylethyl, phenyl, halophenyl, such as 2-fluorophenyl, 2-chlorophenyl, 2-bromophenyl, 3-fluorophenyl, 4-fluorophenyl, 4-chlorophenyl or 4-bromophenyl, dihalophenyl, such as 2,3-dichlorophenyl, 2-chloro-3-fluorophenyl, 2,4-dichlorophenyl, 2-chloro-4-fluorophenyl, 2-bromo-4-fluorophenyl, 2-bromo-4-chlorophenyl, 2,6-difluorophenyl or 2,6-dichlorophenyl, $C_1$-$C_4$-alkylphenyl, such as 2-methylphenyl, 4-methylphenyl or 4-tert-butylphenyl, $C_1$-$C_4$-haloalkylphenyl, such as 4-trifluoromethylphenyl, $C_1$-$C_4$-alkoxyphenyl, such as 2-methoxyphenyl, 4-methoxyphenyl or 4-tert-butoxyphenyl, or 2-cyanophenyl, 4-cyanophenyl, 2-chloro-4-cyanophenyl, 2-cyano-4-chlorophenyl, 2-nitrophenyl, 4-nitrophenyl, 2-chloro-4-nitrophenyl, biphenyl, 4-phenoxyphenyl or 4-(4'-chlorophenoxy)-phenyl, phenylalkyl, such as benzyl, 2-methylbenzyl, 2-fluorobenzyl, 2-chlorobenzyl, 3-fluorobenzyl, 4-fluorobenzyl, 4-chlorobenzyl, 2,4-dichlorobenzyl, phenethyl, 4-fluorophenethyl or 4-chlorophenethyl;

$C_5$- or $C_6$-hetaryl which contains 3 nitrogen atoms, not more than 2 of which may be adjacent, or up to 2 of the following hetero atoms: oxygen, sulfur and/or nitrogen, where 2 oxygen and/or sulfur atoms may not be adjacent, and which furthermore may carry a phenyl or phenoxy substituent having, if required, from 1 to 3 halogen atoms, such as fluorine, chlorine or bromine, or up to 2 of the radicals stated for the phenyl, naphthyl or cycloalkyl groups; preferred groups are furan-2-yl, thien-3-yl, 2-chlorothien-3-yl, 3-bromothien-2-yl, pyrrol-2-yl, pyrazol-2-yl, isoxazol-5-yl, 3-isopropyl isoxazol-5-yl, 3-phenylisoxazol-5-yl, pyrid-3-yl and pyrimid-2-yl.

Particularly preferred compounds I and III are shown in Tables A and B.

The 5-(1,2,4-triazol-1-ylmethyl)-isoxazolines I are obtainable in various ways, preferably by converting aldehyde oximes IIa in a conventional manner (cf. DE-A 27 54 832) with hypochlorites into their nitrile oxides and then reacting the latter with a 2-(1,2,4-triazol-1-ylmethyl)-alkene III:

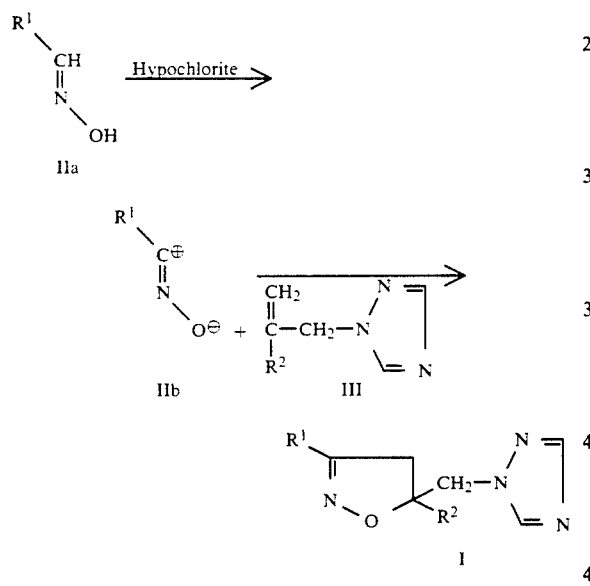

The reaction is preferably carried out in alkaline solution, particularly preferably in a bufferred two-phase system of water and an inert organic solvent, in particular methylene chloride.

Advantageously, the oxime IIa and the alkene III are initially taken and nitrile oxide IIb is produced in situ by adding an alkali metal or alkaline earth metal hypochlorite, in particular sodium hypochlorite or potassium hypochlorite.

The educts IIa and III and the hypochlorite are usually used in a roughly stoichiometric ratio, but an excess of one or other component, for example up to 30%, may also be advantageous in some cases.

In general, the reaction temperature is from −80° C. to the boiling point of the solvent or solvent mixture, in particular from −20° to 40° C.

The reaction is advantageously carried out under atmospheric pressure. Reduced or superatmospheric pressure is possible but generally has no advantages.

The 2-(1,2,4-triazol-1-ylmethyl)-alkenes III are obtainable in various ways, preferably by the following methods:

a) Wittig reaction of methylenephosphonium ylides IV with 1,2,4-triazol-1-ylmethyl ketones V:

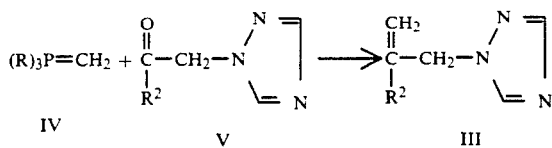

R is an aromatic or $C_6$-cycloaliphatic radical, in particular phenyl.

Advantageously, a methylenetriaryl- or methylene-tri-($C_6$-cycloalkyl)-phosphonium halide, preferably the chloride or bromide, is converted with a strong base in a conventional manner into the phosphonium ylide IV, and the latter is reacted in situ with the ketone V.

The reaction is usually carried out in an inert solvent, for example in an aliphatic hydrocarbon, such as hexane or cyclohexane, in an aromatic hydrocarbon, such as benzene, toluene or o-, m- or p-xylene, in a chlorohydrocarbon, such as methylene chloride, carbon tetrachloride or chlorobenzene, in an ether, such as diethyl ether, methyl tert-butyl ether or tetrahydrofuran, or in a sulfoxide, such as dimethyl sulfoxide.

Examples of suitable bases are alkali metal alcoholates, such as potassium tert-butylate, amides, such as sodium amide or lithium diisopropylamide or hydrides, such as sodium hydride or potassium hydride.

Advantageously, the phosphonium halides, bases and ketones V are used in a roughly stoichiometric ratio, or a slight excess of one or other component, not more than about 10 mol %, is employed.

In general, the reaction temperature is from −50° C. to the reflux temperature of the solvent, in particular from 20° to 80° C.

Regarding the pressure, the above information for the preparation of the isoxazolines I is applicable.

b) Reaction of halomethylalkenes VI with 1,2,4-triazole in the presence of a base:

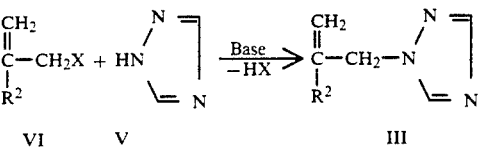

X=halogen, preferably chlorine or bromine.

The synthesis is usually carried out in a conventional manner [cf. J. Org. Chem. USSR 19 (1983), 1552]by converting the triazole by means of a base into its anion and then reacting the latter with a halomethylalkene VI.

Suitable bases are alkali metal alcoholates, such as potassium ethylate, or alkali metal hydroxides, such as potassium hydroxide.

The reaction is advantageously carried out in a suitable inert solvent, for example in ethanol (particularly when an ethylate is used as the base) or in dimethylformamide.

In general, all reactants are used in stoichiometric amounts, but an excess of one or other component may also be advisable. For example, an excess of triazole, for example from 1 to 2 times the amount, based on the amount of base, or from 1 to 5, in particular from 1 to 4, times the amount, based on the amount of halomethylalkene VI, can be used.

In addition, ammonium iodide can be added as a catalyst, for example in an equimolar amount or in an excess of not more than about 20%, based on the amount of halomethylalkene VI.

The reaction temperature is not critical. In general, the reaction is carried out at from 0° to 120° C., in particular from 20° to 100° C., particularly preferably from 20° to 30° C.

Since the reaction is not pressure-dependent, it is preferably carried out at atmospheric pressure.

The halomethylalkenes VI can be prepared from the corresponding hydroxymethylalkenes by conventional methods. For the preparation of hydroxymethylalkenes, reference may be made, for example, to J. Organomet. Chem. 168 (1979), 1.

The novel compounds I contain one or more centers of asymmetry. They act as racemates, the form in which they are obtained in most preparation processes, but can, if required, also be separated into pure isomers by the conventional methods, for example by chromatography over an optically active adsorbent.

Suitable acid addition salts are the salts of acids which do not adversely affect the fungicidal action of I, for example the hydrochlorides, hydrobromides, sulfates, nitrates, phosphates, oxalates or dodecylbenzenesulfonates.

Suitable metal complexes are complexes of copper, of zinc, of tin, of manganese, of iron, of cobalt or of nickel. The complexes are preferably prepared from the free bases I and salts of the metals with mineral acids, for example the chlorides or sulfates.

The 5-(1,2,4-triazol-1-ylmethyl)-isoxazolines I are suitable as fungicides and for regulating plant growth.

The novel fungicidal and growth-regulating 5-(1,2,4-triazol-1-ylmethyl)-isoxazolines and the agents containing them can be used, for example, in the form of directly sprayable solutions, powders, suspensions, including concentrated aqueous, oily or other suspensions or dispersions, emulsions, oil dispersions, pastes, dusting agents, broadcasting agents or granules, by spraying, atomizing, dusting, broadcasting or pouring. The application forms depend entirely on the intended uses; they should in any case ensure very fine distribution of the novel active ingredients.

Usually, the plants are sprayed or dusted with the active ingredients or the seeds of the plants are treated with the active ingredients.

The formulations are prepared in a known manner, for example by extending the active ingredient with solvents and/or carriers, if required with the use of emulsifiers and dispersants; where water is used as a diluent, other organic solvents may also be used as auxiliary solvents. Suitable assistants for this purpose are essentially solvents such as aromatics (eg. xylene), chlorinated aromatics (eg. chlorobenzenes), paraffins (eg. mineral oil fractions), alcohols (eg. methanol and butanol), ketones (eg. cyclohexanone), amines (eg. ethanolamine and dimethylformamide) and water; carriers such as ground natural minerals (eg. kaolins, aluminas, talc and chalk) and ground synthetic minerals (eg. finely divided silica and silicates); emulsifiers, such as nonionic and anionic emulsifiers (eg. polyoxyethylene fatty alcohol ethers, alkylsulfonates and arylsulfonates) and dispersants, such as ligninsulfite waste liquors and methylcellulose.

Suitable surfactants are the alkali metal, alkaline earth metal and ammonium salts of aromatic sulfonic acids, for example lignin-, phenol-, naphthalene- and dibutylnaphthalenesulfonic acids, and of fatty acids, alkyl- and alkylarylsulfonates, alkylsulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ethers, ethoxylated isooctyl-, octyl- or nonylphenol, alkylphenol and tributylphenyl polyglycol ethers, alkylaryl polyether alcohols, isotridecyl alcohol, fatty alcohol ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, broadcasting agents and dusting agents can be prepared by mixing or milling the active substances together with a solid carrier.

Granules, for example coated, impregnated and homogeneous granules, can be prepared by binding the active ingredients to solid carriers. Solid carriers are mineral earths, such as silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as cereal meal, ground bark, woodmeal and nutshell meal, cellulose powder, or other solid carriers.

Examples of such formulations are:

I. A solution of 90 parts by weight of compound No. A.01 and 10 parts by weight of N-methyl-α-pyrrolidone, which is suitable for use in the form of very small drops;

II. A mixture of 20 parts by weight of compound No. A.34, 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid, 5 parts by weight of the adduct of 40 moles of ethylene oxide with 1 mole of castor oil; a dispersion is obtained by finely distributing the solution in water;

III. An aqueous dispersion of 20 parts by weight of compound No. A.37, 40 parts by weight of cyclo-hexanone, 30 parts by weight of isobutanol, 20 parts by weight of the adduct of 40 moles of ethylene oxide with 1 mole of castor oil;

IV. An aqueous dispersion of 20 parts by weight of compound No. A.38, 25 parts by weight of cyclo-hexanol, 65 parts by weight of a mineral oil fraction boiling within a range from 210° to 280° C. and 10 parts by weight of the adduct of 40 moles of ethylene oxide with 1 mole of castor oil;

V. A mixture, milled in a hammer mill, of 80 parts by weight of compound No. A.39, 3 parts by weight of the sodium salt of diisobutylnaphthalene-α-sulfonic acid, 10 parts by weight of the sodium salt of a ligninsulfonic acid obtained from a sulfite waste liquor and 7 parts by weight of silica gel powder; a spray liquor is obtained by finely distributing the mixture in water;

VI. An intimate mixture of 3 parts by weight of compound No. A.53 and 97 parts by weight of finely divided kaolin; this dusting agent contains 3% by weight of active ingredient;

VII. An intimate mixture of 30 parts by weight of compound No. A.54, 92 parts by weight of silica gel powder and 8 parts by weight of liquid paraffin which has been sprayed onto the surface of the silica gel; this formulation imparts good adhesion to the active ingredient;
VIII. A stable aqueous dispersion of 40 parts by weight of compound No. A.58, 10 parts by weight of the sodium salt of a phenolsulfonic acid/urea/formaldehyde condensate, 2 parts by weight of silica gel and 48 parts by weight of water, which dispersion can be further diluted;
IX. A stable oily dispersion of 20 parts by weight of compound No. A.60, 2 parts by weight of the calcium salt of dodecylbenzenesulfonic acid, 8 parts by weight of a fatty alcohol polyglycol ether, 20 parts by weight of the sodium salt of a phenolsulfonic acid-/urea/formaldehyde condensate and 68 parts by weight of a paraffinic mineral oil.

The 5-(1,2,4-triazol-1-ylmethyl)-isoxazolines I have excellent activity against a broad spectrum of phytopathogenic fungi, in particular from the class consisting of the Ascomycetes and Basidiomycetes. Some of them have systemic activity and can be used as foliage and soil fungicides.

They are particularly important for controlling a large number of fungi on various crops, such as wheat, rye, barley, oats, rice, corn, grass, cotton, soybean, coffee, sugar cane, grapevines, fruit trees, ornamentals and vegetable plants, such as cucumbers, beans and cucurbitaceae, and on the seeds of these plants.

Application is effected before or after infection of the plants or seeds with the fungi.

The compounds I are particularly suitable for controlling the following plant diseases:
*Erysiphe graminis* (powdery mildew) in cereals,
*Erysiphe cichoracearum* and *Sphaerotheca fuliginea* in cucurbitaceae,
*Podosphaera leucotricha* on apples,
*Uncinula necator* on grapevines,
*Puccinia species* on cereals,
*Rhizoctonia species* on cotton and lawns,
*Ustilago species* on cereals and sugar cane,
*Venturia inaequalis* (scab) on apples,
*Helminthosporium species* on cereals,
*Septoria nodorum* on wheat,
*Botrytis cinerea* (gray mold) on strawberries and grapevines,
*Cercospora arachidicola* on peanuts,
*Pseudocercosporella herpotrichoides* on wheat and barley,
*Pyricularia oryzae* on rice,
*Phytophthora infestans* on potatoes and tomatoes,
*Fusarium* and *Verticillium species* on various plants,
*Plasmopara viticola* on gravepines and
*Alternaria species* on vegetables and fruit.

The fungicides contain in general from 0.1 to 95, preferably from 0.5 to 90, % by weight of active ingredient.

The application rates are from 0.02 to 3 kg of active ingredient per ha, depending on the type of effect desired. The novel compounds can also be used in material protection, for example against *Paecilomyces variotii*.

In the application form as fungicides, the novel agents may also be present together with other active ingredients, for example with herbicides, insecticides, growth regulators, fungicides or fertilizers.

When mixed with fungicides, an increase in the fungicidal action spectrum is obtained in many cases.

The following list of fungicides together with which the novel compounds can be applied is intended to illustrate the possible combinations but not to impose restrictions:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N-ethylenebisdithiocarbamate,
ammonia complex of zinc N,N'-propylenebisdithiocarbamate, zinc N,N'-propylenebisdithiocarbamate and N,N'-propylenebis-(thiocarbamoyl) disulfide;
nitro derivatives, such as
dinitro-(1-methylheptyl)-phenyl crotonate,
2-sec-butyl-4,6-dinitrophenyl 3,3-dimethylacrylate,
2-sec-butyl-4,6-dinitrophenyl isopropyl carbonate and diisopropyl 5-nitroisophthalate;
heterocyclic substances, such as
2-heptadecyl-2-imidazoline acetate,
2,4-dichloro-6-(o-chloroanilino)-s-triazine,
0,0-diethyl phthalimidophosphonothioate,
5-amino-1-[bis-(dimethylamino)-phosphinyl]-3-phenyl-1,2,4-triazole,
2,3-dicyano-1,4-dithioanthraquinone,
2-thio-1,3-dithiolo[4,5-b]quinoxaline,
methyl 1-(butylcarbamoyl)-2-benzimidazolecarbamate,
2-methoxycarbonylaminobenzimidazole,
2-(fur-2-yl)-benzimidazole,
2-(thiazol-4-yl)-benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
pyridine-2-thio-1-oxide,
8-hydroxyquinoline and its copper salt,
2,3-dihydro-5-carboxanilido-6-methyl-1,4-oxathiine,
2,3-dihydro-5-carboxanilido-6-methyl-1,4-oxathiine 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethylfuran-3-carboxylic acid cyclohexylamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethyl acetal,
piperazine-1,4-diylbis-(1-(2,2,2-trichloroethyl)formamide),
1-(3,4-dichloroanilino)-1-formylamino-2,2,2-trichoroethane,
2,6-dimethyl-N-tridecylmorpholine and its salts,
2,6-dimethyl-N-cyclododecylmorpholine and its salts,
N-[3-(p-tert-butylphenyl)-2-methylpropyl]-cis-2,6-dimethylmorpholine,
N-[3-(p-tert-butylphenyl)-2-methylpropyl]-piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidine methanol, 5-butyl-2-dimethylamino-4-hydroxy-6-methylpyrimidine, bis-(p-chlorophenyl)-3-pyridinemethanol, 1,2-bis-(3-ethoxycarbonyl-2-thioureido)-benzene and 1,2-bis-(3-methoxycarbonyl)-2-thioureido)-benzene, and various fungicides, such as dodecylguanidine acetate, 3-[3-(3,5-dimethyl-2-oxycyclohexyl)-2-hydroxyethyl]-glutarimide, hexachlorobenzene, methyl DL-N-(2,6-dimethylphenyl)-N-2-furoylalaninate, methyl DL-N-(2,6-dimethylphenyl)-N-(2'-methoxyacetyl)alaninate, N-(2,6-dimethylphenyl)-N-chloroacetyl-D,L-2-aminobutyrolactone, methyl DL-N-(2,6-dimethylphenyl)-N-(phenylacetyl)alaninate, 5-methyl-5-vinyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl)-pentyl]-1H-1,2,4-triazole, 2,4-difluoro-α-(1H-1,2,4-triazol-1-ylmethyl)-benzhydryl alcohol, N-(3-chloro-2,6-dinitro-4-trifluoromethylphenyl-5-trifluoromethyl-3-chloro-2-aminopyridine and 1-((bis-(4-fluorophenyl)-methylsilyl)-methyl)-1H-1,2,4-triazole.

Apart from their action against fungi, 5-(1,2,4-triazol-1-ylmethyl)-isoxazolines can also influence the various stages of development of a plant and can therefore be used as growth regulators. The variety of activity of the plant growth regulators is dependent in particular
a) on the plant species and variety,
b) on the time of application, based on the stage of development of the plant, and on the season,
c) on the place and method of application (for example seed dressing, soil treatment, foliage application or trunk injection in the case of trees),
d) on climatic factors (for example temperature, amount of precipitation and also length of day and light density),
e) on the soil characteristics (including fertilizer application),
f) on the formulation or application form of the active ingredient and
g) on the concentrations of active substance used.

Of the various possible applications of the novel plant growth regulators of the formula I in plant cultivation, in agriculture and in horticulture, some are stated below.

A. The compounds which can be used according to the invention can be employed for greatly inhibiting the vegetative growth of the plants, which manifests itself in particular in a reduction in the length of growth. The treated plants accordingly exhibit squat growth; a darker leaf coloration is also observed.

Reduced intensity of growth of grasses along road edges, hedges and canal banks and on lawn areas, such as parks, sports grounds, orchards, ornamental lawns and airfields, is advantageous in practice, so that the labor-intensive and expensive cutting of lawns can be reduced.

The increase in the strength of crops which are susceptible to lodging, such as cereals, corn, sunflowers and soybean, is also of economic interest. The resulting shortening and strengthening of the stem reduce or eliminate the danger of lodging (of bending) of plants under unfavorable weather conditions prior to harvesting.

The application of growth regulators for inhibiting the length of growth and for changing the time of ripening in the case of cotton is also important. Completely mechanized harvesting of this important crop is thus possible.

In the case of fruit trees and other trees, it is possible to reduce cutting costs by means of the growth regulators. Furthermore, the alternance of fruit trees can be broken by growth regulators.

By using growth regulators, it is also possible to increase or inhibit the lateral branching of the plants. This is of interest if, for example in the case of tobacco plants, it is intended to inhibit the formation of side shoots in favor of leaf growth.

Growth regulators can also be used to achieve a considerable increase in frost resistance, for example in winter rape. On the one hand, the length of growth and the development of a leaf or plant mass which is too luxuriant (therefore particularly susceptible to frost) are inhibited. On the other hand, the young rape plants are held back in the vegetative stage of development after sowing and before the onset of the winter frosts, in spite of favorable growth conditions. This also eliminates the frost risk for plants which tend to undergo a premature decline in the inhibition of blooming and to change over to the generative phase. In other crops too, for example winter cereals, it is advantageous if the stocks are thoroughly tillered in the fall as a result of treatment with novel compounds but do not begin the winter with too luxuriant a growth. This makes it possible to prevent high sensitivity to frost and, owing to the relatively small leaf or plant mass, attack by various diseases (for example fungal disease). The inhibition of vegetative growth furthermore permits denser planting of the soil in the case of many crops, so that it is possible to achieve a higher yield based on the soil area.

B. The growth regulators make it possible to achieve higher yields both of plant parts and of plant ingredients. For example, it is possible to induce the growth of larger amounts of buds, blooms, leaves, fruits, seeds, roots and tubers, to increase the content of sugar in sugarbeets, sugar cane and citrus fruits, to increase the protein content of cereals or soybean or to stimulate rubber trees to produce greater latex flow.

The compounds of the formula I can increase yields by intervening in the plant metabolism or by promoting or inhibiting vegetative and/or generative growth.

C. Finally, plant growth regulators can be used both for shortening or increasing the stages of development and for accelerating or retarding ripening of the harvested plant parts before or after the harvest.

For example, easier harvesting is of economic interest and is permitted by concentrated dropping or reduced adhesion to the tree in the case of citrus fruits, olives or other species and varieties of pomes, drupes and hardshell fruit. The same mechanism, i.e. the promotion of the formation of abscission tissue between fruit or leaf part and shoot part of the plant, is also essential for readily controllable defoliation of crops such as cotton.

D. Growth regulators can also be used to reduce the water consumption of plants. This is particularly important for agricultural areas which have to be artificially irrigated at high expense, for example in arid or semi-arid regions. By using the novel substances, it is possible to reduce the intensity of irrigation and hence to carry out more economical farming. Under the influence of growth regulators, there is better utilization of the available water because, inter alia, the extent of opening of the stomata is reduced, a thicker epidermis and a thicker cuticula are formed, the root penetration of the soil is improved and the microclimate in the plant stock is advantageously influenced by more compact growth.

The growth regulators of the formula I which are to be used according to the invention can be fed to the crops both via the seed (as seed dressings) and via the soil, i.e. through the roots and, particularly preferably, by spraying over the foliage.

Because of the high toleration by plants, the application rate can be greatly varied.

The application rates of active ingredient when used as a growth regulator vary depending on the aim of control, the season, the target plants and the stages of growth.

To extend the action spectrum and to achieve synergistic effects, the novel compounds I can be mixed with, and applied together with, a large number of members of other groups of growth-regulating active ingredients.

It may also be useful to apply the compounds I, alone or in combination with herbicides or fungicides, also as a mixture with other crop protection agents, for example with pesticides or bactericides. The miscibility with mineral salt solutions which are used for eliminating nutrient and trace element deficiencies is also of interest. Nonphytotoxic oils and oil concentrates can also be added.

PREPARATION EXAMPLES

EXAMPLE 1

(Table Example A.34)

3-(4-Chlorophenyl)-5-tert-butyl-5-(1,2,4-triazol-1-ylmethyl)-isoxazoline

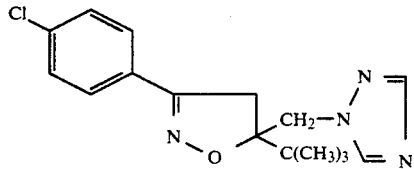

2.6 g (17 mmol) of 4-chlorobenzaldehyde oxime and 3.3 g (20 mmol) of 2-(1,2,4-triazol-1-ylmethyl)-3,3-dimethylbut-1-ene were added to a two-phase system consisting of 15 ml of methylene chloride and 15 ml of a phosphate buffer [containing 0.3 g (1.7 mmol) of Na₂HPO₄.2H₂O and 0.25 g (1.6 mmol) of NaH₂PO₄.2H₂O]. 12.6 g (22 mmol) of a 13% strength aqueous sodium hypochlorite solution were added dropwise to this mixture at about 20° C. and stirring was continued for 3 hours after the end of the addition. Thereafter, the organic phase was diluted with 150 ml of methylene chloride, washed 3 times with water after phase separation and worked up in a conventional manner to obtain the product. The crude product was purified by stirring with diisopropyl ether.

Yield: 53.5%.

Intermediate 1a (Table Example B.01)

2-(1,2,4-Triazol-1-ylmethyl)-3,3-dimethylbut-1-ene

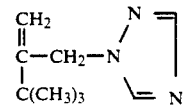

A mixture of 236.6 g (0.66 mol) of methyltriphenylphosphonium bromide, 70.6 g (0.63 mol) of potassium tert-butylate and 700 g of tetrahydrofuran was refluxed for 1 hour. 100 g (0.60 mol) of triazolylpinacolone were then added at about 20° C and the mixture was heated for a further 2 hours at 60° C. The solvent was removed and the crude product was then taken up in methyl tert-butyl ether. The ether phase was washed, dried and evaporated down. The residue was taken up in pentane and the solid triphenylphosphine oxide was filtered off. The product was then precipitated as the nitrate salt by adding nitric acid, and was isolated. After the addition of sodium hydroxide solution, the free base was obtained as a slowly crystallizing, colorless oil from the purified salt.

Yield: 60.6%.

EXAMPLE 2

(Table Example A.46)

3-(2-Chlorophenyl)-5-benzyl-5-(1,2,4-triazol-1-ylmethyl)-isoxazoline

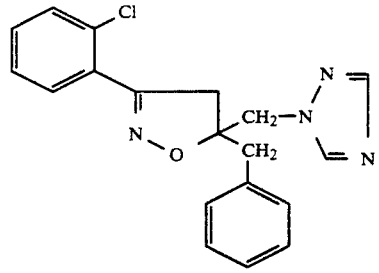

2.58 g (13 mmol) of 2-(1,2,4-triazol-1-ylmethyl)3-phenylprop-1-ene were reacted with 2.02 g (13 mmol) of 2-chlorobenzaldehyde oxime similarly to Example A in a two-phase system (consisting of 40 ml of methylene chloride and 40 ml of phosphate buffer) in the presence of 8.7 g (15 mmol) of 13% strength aqueous sodium hypochlorite solution. After the end of the addition of hypochlorite, the mixture was stirred for a further 16 hours and was worked up to obtain the product. Yield: 87%.

Intermediate 2a
2-Chloromethyl-3-phenylprop-1-ene

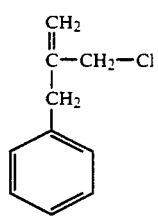

148 g (1 mol) of 2-hydroxymethyl-3-phenylprop-1-ene were added dropwise at 40° C to a mixture of 357 g (3 mol) of thionyl chloride, 0.5 g (4 mmol) of dimethylaminopyridine and 1 l of methylene chloride in the course of 2 hours. Thereafter, the mixture was refluxed for 3 hours and was then poured onto 1.5 l of ice water and neutralized with sodium hydroxide solution. The aqueous phase was separated off and extracted 3 times with methylene chloride, after which the combined organic phases were worked up in a conventional manner to obtain the product. Yield: 99% (colorless oil); $^1$H-NMR (in CDCl$_3$, TMS as standard): 3.5 ppm (s, 2H), 3.9 ppm (s, 2H), 5.2 ppm (s, 1H), 7.1–4 ppm (m, 1H).

Intermediate 2b (Table Example B.02)
2-(1,2,4-Triazol-1-ylmethyl)-3-phenylprop-1-ene

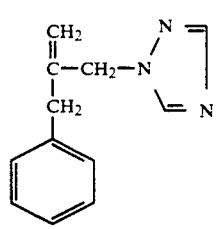

A solution of 33.3 g (0.2 mol) of 2-chloromethyl-3-phenylprop-1-ene in 50 ml of dimethylformamide was added dropwise to a mixture of 22.4 g (0.4 mol) of potassium hydroxide powder, 55.2 g (0.8 mol) of 1,2,4-triazole and 100 ml of dimethylformamide at 20° C. After the end of the addition, the reaction mixture was stirred for a further 16 hours, then diluted with 700 ml of methyl tert-butyl ether, washed four times with water and then worked up in a conventional manner to obtain the product. Yield: 69% (pale yellow oil); $^1$H-NMR (in CDCl$_3$, TMS as standard): 3.3 ppm (s, 2H), 4.7 ppm (s, 2H), 5.0 ppm (s, 1H), 5.1 ppm (s, 1H), 7.0–4 ppm (s, 5H), 7.95 ppm (s, 1H), 8.0 ppm (s, 1H).

The physical data of the end products I and of the novel 2-(1,2,4-triazol-1-ylmethyl)-alkenes III are shown in Tables A and B, which also list further compounds I and III which were prepared by the same methods.

TABLE A

| No. | R$^1$ | R$^2$ | Physical data (NMR in CDCl$_3$ [ppm]; TMS as standard) |
|---|---|---|---|
| A.01 | Cyclopentyl | Methyl | Oil, NMR: 1.4(s, 3H), 2.7(d, 1H), 3.1(d, 1H), 4.3(s, 2H) |
| A.02 | 4-Fluorophenyl | Hydrogen | Oil, NMR: 3.3(dd, 1H), 3.5(dd, 1H), 4.4(d, 1H) |
| A.03 | 4-Fluorophenyl | Methyl | Oil, NMR: 1.5(s, 3H), 3.1(d, 1H), 3.5(d, 1H), 4.4(s,2H) |
| A.04 | 4-Chlorophenyl | Methyl | Oil, NMR: 1.5(s, 3H), 3.1(d, 1H), 3.5(d, 1H, 4.4(s, 2H) |
| A.05 | 2-Chlorophenyl | Methyl | Oil, NMR: 1.5(s, 3H), 3.3(d, 1H), 3.6(d, 1H), 4.4(s, 2H) |
| A.06 | 2-Chlorophenyl | Hydrogen | Oil, NMR: 3.4(dd, 1H), 3.7(dd, 1H), 4.4(d, 2H) |
| A.07 | 2-Fluorophenyl | Hydrogen | Oil, NMR: 3.4(ddd, 1H), 3.6(ddd, 1H), 4.4(d, 2H) |
| A.08 | 2-Fluorophenyl | Methyl | Oil, NMR: 1.5(s, 3H), 3.2(dd, 1H), 4.4(s, 2H) |
| A.09 | 3-Fluorophenyl | Methyl | Oil, NMR: 1.5(s, 3H), 3.1(d, 1H), 3.5(d, 1H), 4.4(s, 2H) |
| A.10 | 3-Chlorophenyl | Methyl | Oil, NMR: 1.5(d, 3H), 3.1(d, 1H), 3.5(d, 1H), 4.4(s, 2H) |
| A.11 | 2,4-Dichlorophenyl | Methyl | Oil, NMR: 1.5(s, 3H), 3.3(d, 1H), 3.6(d, 1H), 4.4(d, 2H) |
| A.12 | Pyrid-2-yl | Methyl | Oil, NMR: 1.5(s, 3H), 3.3(d, 1H), 3.6(d, 1H), 4.4(d, 2H) |
| A.13 | Pyrid-2-yl | Hydrogen | Oil, NMR: 3.4(dd, 1H), 3.7(dd, 1H), 4.4(d, 2H) |
| A.14 | 4-Fluorobenzyl | Hydrogen | Oil, NMR: 2.8(dd, 1H), 3.0(dd, 1H), 4.2–4(m, 2H) |
| A.15 | 4-Fluorobenzyl | Methyl | Oil, NMR: 1.4(s, 3H), 2.6(d, 1H), 3.0(d, 1H), 4.3(s, 2H) |
| A.16 | tert-Butyl | Methyl | Oil, NMR: 1.5(s, 1H), 2.7(d, 1H), 3.1(d, 1H), 4.3(s, 2H) |
| A.17 | tert-Butyl | Hydrogen | Oil, NMR: 2.9(d, 1H), 3.1(d, 1H), 4.2–4(m, 2H) |
| A.18 | 5,5-Dimethyl-1,3-dioxan-2-yl | Hydrogen | Oil, NMR: 3.0(dd, 1H), 3.3(dd, 1H), 4.3(d, 2H) |
| A.19 | 5,5-Dimethyl-1,3-dioxan-2-yl | Methyl | Oil, NMR: 1.4(s, 3H), 2.9(d, 1H), 3.2(d, 1H), 4.3(s, 2H) |
| A.20 | 4-Fluorophenyl | Phenyl | Oil, NMR: 3.5(d, 1H), 4.0(d, 1H), 4.6(d, 1H), 4.7(d, 1H) |
| A.21 | 2,4-Dichlorophenyl | Phenyl | m.p.: 116° C. |
| A.22 | 2-Chlorophenyl | Phenyl | m.p.: 157–58° C. |
| A.23 | 4-Chlorophenyl | Phenyl | m.p.: 98° C. |
| A.24 | 2-Fluorophenyl | Phenyl | m.p.: 157–58° C. |
| A.25 | Phenyl | Phenyl | m.p.: 133–5° C. |
| A.26 | 3-Fluorophenyl | Phenyl | m.p.: 156–8° C. |
| A.27 | 4-Fluorophenyl | Phenyl | m.p.: 103–5° C. |
| A.28 | n-Propyl | Phenyl | Oil, NMR: 3.1(d, 1H), 3.5(d, 1H), 4.47(d, 1H), 4.55(d, 1H) |
| A.29 | tert-Butyl | Phenyl | m.p.: 125–7° C. |
| A.30 | Cyclopropyl | Phenyl | m.p.: 104–5° C. |
| A.31 | Ethyl | Phenyl | m.p.: 75–7° C. |
| A.32 | Isopropyl | Phenyl | m.p.: 87–8° C. |
| A.33 | 2-Chlorophenyl | tert-Butyl | m.p.: 104° C. |
| A.34 | 4-Chlorophenyl | tert-Butyl | m.p.: 157° C.; NMR: 1.12(s, 9H), 3.23(d, 1H), 3.43(d, 1H) 4.5(d, 1H), 4.6(d, 1H), 7.3(d, 2H), 7.38(s, 2H) 7.72(s, 1H), 8.25(s, 1H) |
| A.35 | Phenyl | tert-Butyl | m.p.: 150° C. |

TABLE A-continued

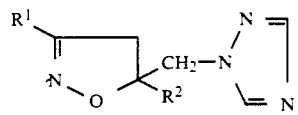

| No. | R¹ | R² | Physical data (NMR in CDCl₃ [ppm]; TMS as standard) |
|---|---|---|---|
| A.36 | 2-Fluorophenyl | tert-Butyl | m.p.: 115–7° C. |
| A.37 | 4-Fluorophenyl | tert-Butyl | m.p.: 165° C. |
| A.38 | 3-Fluorophenyl | tert-Butyl | m.p.: 162° C. |
| A.39 | 4-Fluorophenyl | 4-Fluorophenyl | m.p.: 98–100° C. |
| A.40 | 4-Fluorophenyl | tert-Butyl | m.p.: 109° C. |
| A.41 | tert-Butyl | tert-Butyl | m.p.: 138–40° C. |
| A.42 | 2,4-Dichlorophenyl | tert-Butyl | m.p.: 93° C. |
| A.43 | 2,6-Difluorophenyl | tert-Butyl | Oil, NMR: 3.3(d, 1H), 3.4(d, 1H), 4.5(d, 1H), 4.6(d, 1H) |
| A.44 | 2-Methylphenyl | tert-Butyl | Oil, NMR: 3.3(d, 1H), 3.5(d, 1H), 4.5(d, 1H), 4.6(d, 1H) |
| A.45 | 4-Fluorophenyl | Benzyl | Oil, NMR: 3.2(d, 1H), 3.4(d, 1H), 4.4(s, 2H) |
| A.46 | 2-Chlorophenyl | Benzyl | Oil, NMR: 3.1(d, 1H), 3.15(d, 1H), 3.4(d, 1H), 3.5(d, 1H), 4.5(s, 2H), 7.0–5(m, 9H), 7.9(s, 1H), 8.3(s, 1H) |
| A.47 | 2,4-Dichlorophenyl | Benzyl | Oil, NMR: 3.3(d, 1H), 3.5(d, 1H), 4.5(s, 2H) |
| A.48 | n-Propyl | tert-Butyl | m.p.: 54° C. |
| A.49 | Cyclopropyl | tert-Butyl | m.p.: 102° C. |
| A.50 | n-Butyl | tert-Butyl | m.p.: 49° C. |
| A.51 | Isopropyl | tert-Butyl | m.p.: 110° C. |
| A.52 | 2,4-Dichlorophenyl | 4-Fluorophenyl | m.p.: 112° C. |
| A.53 | 2-Chlorophenyl | 4-Fluorophenyl | m.p.: 115° C. (decomposition) |
| A.54 | 4-Chlorophenyl | 4-Fluorophenyl | m.p.: 125° C. (decomposition) |
| A.55 | Phenyl | 4-Fluorophenyl | m.p.: 145° C. (decomposition) |
| A.56 | n-Butyl | 4-Fluorophenyl | m.p.: 78° C. |
| A.57 | tert-Butyl | 2,4-Dichlorophenyl | m.p.: 114° C. |
| A.58 | 2-Fluorophenyl | 4-Fluorophenyl | m.p.: 120° C. |
| A.59 | 3-Fluorophenyl | 4-Fluorophenyl | m.p.: 149° C. |
| A.60 | 4-Fluorophenyl | 4-Fluorophenyl | m.p.: 90–4° C. |
| A.61 | n-Propyl | 4-Fluorophenyl | m.p.: 72° C. |
| A.62 | tert-Butyl | 4-Fluorophenyl | m.p.: 131° C. |
| A.63 | Cyclopropyl | 4-Fluorophenyl | m.p.: 95° C. |
| A.64 | Ethyl | 4-Fluorophenyl | m.p.: 84° C. |
| A.65 | Isopropyl | 4-Fluorophenyl | m.p.: 100° C. |
| A.66 | Ethyl | tert-Butyl | m.p.: 102° C. |
| A.67 | Naphth-2-yl | 4-Fluorophenyl | m.p.: 157–60° C. |
| A.68 | Naphth-1-yl | 4-Fluorophenyl | m.p.: 125° C. |
| A.69 | 2,4-dichlorophenyl | 4-Chlorophenyl | m.p.: 90° C. (decomposition) |
| A.70 | 4-Fluorophenyl | 4-Fluorobenzyl | m.p.: 103° C. |
| A.71 | 4-Fluorophenyl | 4-Chlorophenyl | m.p.: 105° C. |
| A.72 | 4-Chlorophenyl | 4-Fluorobenzyl | m.p.: 101° C. |
| A.73 | 4-Chlorophenyl | 4-Chlorobenzyl | m.p.: 150° C. (decomposition) |
| A.74 | 2,4-Dichlorophenyl | 4-Fluorobenzyl | m.p.: 41° C. |
| A.75 | tert-Butyl | 4-Fluorobenzyl | m.p.: 73° C. |
| A.76 | tert-Butyl | 4-Chlorobenzyl | m.p.: 87° C. |
| A.77 | 4-Fluorophenyl | α-Methylbenzyl | m.p.: 106° C. |
| A.78 | 2,4-Dichlorophenyl | 4-Chlorobenzyl | m.p.: 77° C. |
| A.79 | 2,4-Dichlorophenyl | α-Methylbenzyl | Resin, NMR: 3.2(q, 1H), 3.4(d, 1H), 3.6(d, 1H), 4.3(d, 1H), 4.48(d, 1H) |
| A.80 | 4-Fluorophenyl | 2,4-Dichlorobenzyl | m.p.: 89–91° C. |
| A.81 | 4-Chlorophenyl | 2,4-Dichlorobenzyl | m.p.: 131° C. |
| A.82 | 2,4-Dichlorophenyl | 2,4-Dichlorobenzyl | m.p.: 113° C. |
| A.83 | tert-Butyl | 2,4-Dichlorobenzyl | m.p.: 84° C. |
| A.84 | 4-Fluorophenyl | 2,4-Dichlorophenyl | m.p.: 45° C. |
| A.85 | 2-Chlorophenyl | 2,4-Dichlorophenyl | m.p.: 103° C. |
| A.86 | 2,4-Dichlorophenyl | 2,4-Dichlorophenyl | 52–5° C. |
| A.87 | Isopropyl | 2,4-Dichlorophenyl | Oil, NMR: 3.15(d, 1H), 3.42(d, 1H), 4.47(d, 1H), 4.92(d, 1H) |
| A.88 | 4-Chlorophenyl | 2,4-Dichlorophenyl | m.p.: 52–5° C. |
| A.89 | 4-Methylphenyl | 2,4-Dichlorophenyl | m.p.: 141° C. |
| A.90 | 4-Trifluorophenyl | 2,4-Dichlorophenyl | m.p.: 122° C. |

TABLE B

Novel 2-(1,2,4-triazol-1-ylmethyl)-alkenes III

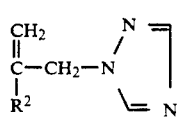

| No. | R² | Physical data (NMR in CDCl₃ [ppm]; TMS as standard) |
|---|---|---|
| B.01 | tert-Butyl | Oil, NMR: 1.15(s, 9H), 4.45(s, 1H), 4.80(s, 2H), 5.10(s, 1H), |

TABLE B-continued

Novel 2-(1,2,4-triazol-1-ylmethyl)-alkenes III

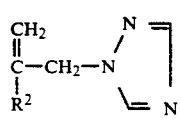

| No. | R² | Physical data (NMR in CDCl₃ [ppm]; TMS as standard) |
|---|---|---|
| | | 7.95(s, 1H), 8.10(s, 1H) |
| B.02 | Benzyl | Oil, NMR: 3.3(s, 2H), 4.7(s, 2H), |

TABLE B-continued

Novel 2-(1,2,4-triazol-1-ylmethyl)-alkenes III

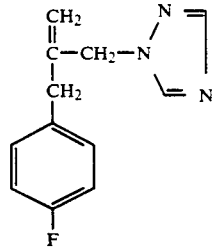

| No. | R² | Physical data (NMR in CDCl₃ [ppm]; TMS as standard) |
|---|---|---|
|  |  | 5.0(s, 1H), 5.1(s, 1H), 7.0–7.4(s, 5H), 7.95(s, 1H) 8.0(s, 1H) |
| B.03 | 4-Fluorobenzyl | NMR: 3.3(s, 2H), 4.7(s, 2H), 5.0(s, 1H), 5.1(s, 1H), 6.9–7.2(m, 4H), 8.0(s, 2H) |
| B.04 | 4-Chlorobenzyl | NMR: 3.3(s, 2H), 4.7(s, 2H), 7.1(d, 2H), 7.3(d, 2H), 8.0(2s, 2H) |
| B.05 | 2-Methylbenzyl |  |
| B.06 | 2,4-Dichlorobenzyl | NMR: 3.4(s, 2H), 4.75(s, 2H), 4.9(s, 1H), 5.05(s, 1H), 7.0–7.5(m, 3H), 8.0(s, 1H), 8.1(s, 1H) |
| B.07 | a-Methylbenzyl | NMR: 1.4(d, 3H), 3.3(q, 1H), 4.6(d, 2H), 5.0(s, 1H), 5.3(s, 1H), 7.1–7.4(m, 5H), 7.9(s, 1H), 7.95(s, 1H) |

EXAMPLE C

Salt of 3-cyclopentyl-5-methyl-5-(1,2,4-triazol-1-ylmethyl)-isoxazoline with nitric acid

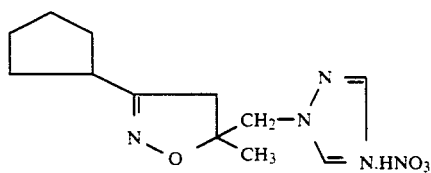

About 20 ml of concentrated nitric acid were added to a solution of 10 g (42.6 mmol) of 3-cyclopentyl-5-methyl-5-(1,2,3-triazol-1-ylmethyl)-isoxazoline in 50 ml of methyl tert-butyl ether at about 20° C. The precipitate formed was then filtered off, washed with methyl tert-butyl ether and dried in a desiccator. Yield: 24%; mp.: 120°–122° C.; ¹H-NMR (in CDCl₃, TMS as standard): 1.3 ppm (s, 3H), 1.35–1.8 ppm (m, 8H), 2.65 ppm (m, 1H), 2 85 ppm (d, 1H), 3.1 ppm (d, 1H), 8.3 ppm (s, 1H), 8.9 ppm (s, 1H), 9.75 ppm (s, broad, 1H).

Use Examples (fungicidal activity)

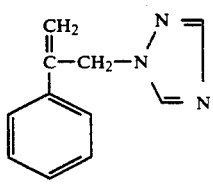

C disclosed in DE-A 28 33 194 (page 6, line 28) and

D disclosed in EP-A 94 167 (compound s, page 26) were used as comparative substances.

EXAMPLE 3

Activity against cucumber mildew

Leaves of pot-grown cucumber seedlings of the Chinesische Schlange variety, in the two-leaf stage, were sprayed with a spore suspension of cucumber mildew. After about 20 hours, the test plants were sprayed to run-off with 0.025% strength aqueous active ingredient formulations which contained 80% of active ingredient (of the active ingredients according to Table Examples A.34, A.37, A.38 and A.54) and 20% of emulsifier, the percentages being based on dry substance, and, after the spray coating had dried on, were placed in a greenhouse at from 20° to 22° C. and from 70 to 80% relative humidity.

After 21 days, the extent of fungal attack was evaluated.

Compared with the control experiment (no treatment, 100% fungal attack) and the known comparative compounds C and D (50% and 100% fungal attack, respectively), the substances A.34, A.37, A.38 and A.54 had a very good fungicidal action (from 0 to 5% fungal attack).

EXAMPLE 4

Activity against Pyrenophora teres

Barley seedlings of the Igri variety, in the two-leaf stage, were sprayed to run-off with 0.05% strength aqueous suspensions which contained 80% of active ingredient (of the active ingredients according to Table Examples A.39, A.53, A.54 and A.58) and 20% of emulsifier, the percentages being based on dry substance. After 24 hours, the plants were infected with a spore suspension of the fungus *Pyrenophora teres* and were placed for 48 hours in a conditioned chamber with high humidity at 18° C.

The plants were then cultivated in a greenhouse at from 20° to 22° C. and 70% relative humidity for a further 5 days. The extent of fungal attack was then evaluated.

Compared with the control experiment (no treatment, 60% fungal attack) and the known comparative compound D (40% fungal attack), it was found that the treated plants exhibited only 0–5% fungal attack.

We claim:

1. A 5-(1,2,4-triazol-1-ylmethyl)-isoxazoline of the formula

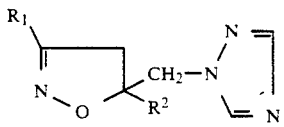

where $R^1$ and $R^2$ are each hydrogen, $C_1$–$C_4$-alkoxy-$C_1$–$C_4$-alkyl, partially or completely halogenated $C_1$–$C_6$-alkyl or $C_1$–$C_6$-alkyl which may carry a $C_3$–$C_8$-cycloalkyl, phenyl or naphthyl radical, or are each $C_3$–$C_8$-cycloalkyl, phenyl or naphthyl, and where the phenyl and naphthyl moieties of the stated groups may furthermore each carry a phenyl or phenoxy radical having up to 3 halogen substituents, or up to 3 of the following radicals: halogen, cyano, nitro, $C_1$–$C_4$-alkyl, partially or completely halogenated $C_1$–$C_4$-alkyl or $C_1$–$C_4$-alkoxy, or $R^1$ and $R^2$ are each furan-2-yl, thien-3-yl, 2-chlorothien-3-yl, 3-bromothien-2-yl, pyrrol-2-yl, pyrazol-2-yl, isoxazol-5-yl, 3-isopropylisoxazol-5-yl, 3-phenylisoxazol-5-yl, pyrid-3-yl or pyrimid-2-yl, and the plant-tolerated mineral acid salts and metal complexes of I.

2. A fungicide containing one or more 5-(1,2,4-triazol-1-ylmethyl)-isoxazoline of the formula I, or a plant-tolerated salt or metal complex thereof as defined in claim 1 and a liquid or solid carrier.

3. A method of controlling fungi, wherein a fungicidal amount of a 5-(1,2,4-triazol-1-ytmethyl)-isoxazoline of the formula I, or a plant-tolerated salt or metal complex thereof as defined in claim 1 is allowed to act on fungi, on materials threatened by fungal attack, on plants, on their habitat or on the seed of the threatened plants.

4. A plant growth regulator containing one or more 5-(1,2,4-triazol-1-ylmethyl)-isoxazoline of the formula I, or a plant-tolerated salt or metal complex thereof as defined in claim 1 and a liquid or solid carrier.

5. A method of regulating plant growth, wherein an amount, effective for regulating plant growth, of a 5-(1,2,4-triazol-1-ylmethyl)-isoxazoline of the formula I, or a plant-tolerated salt or metal complex thereof as defined in claim 1 is allowed to act on the plants, on their habitat or on the seed of the plants.

6. 3-(4-Fluorophenyl)-5-(4-fluorophenyl)-5-(1,2,4-triazol-1-ylmethyl)-isoxazoline.

7. A compound of the formula I as defined in claim 1, wherein $R^1$ is 4-chlorophenyl and $R^2$ is tert.-butyl.

* * * * *

UNITED STATES PATENT AND TRADEMARK OFFICE
CERTIFICATE OF CORRECTION

PATENT NO. : 5,156,669
DATED : October 20, 1992
INVENTOR(S) : ZIERKE et al.

It is certified that error appears in the above-identified patent and that said Letters Patent is hereby corrected as shown below:

<u>In claim 3, col. 20, line 4</u>

"-ytmethyl)-" should read --ylmethyl)- --

Signed and Sealed this

Fifth Day of October, 1993

Attest:

BRUCE LEHMAN

*Attesting Officer*    *Commissioner of Patents and Trademarks*